United States Patent [19]

Lam et al.

[11] 4,352,933
[45] Oct. 5, 1982

[54] CHEMICAL METHODS AND INTERMEDIATES FOR PREPARING SUBSTITUTED PYRIMIDINONES

[75] Inventors: Bing L. Lam, King of Prussia; Lendon N. Pridgen, Audubon, both of Pa.

[73] Assignee: Smithkline Beckman Corporation, Philadelphia, Pa.

[21] Appl. No.: 232,105

[22] Filed: Feb. 6, 1981

[51] Int. Cl.$^3$ .......................................... C07D 405/14
[52] U.S. Cl. .................................. 544/320; 544/123; 544/295; 544/296; 544/310; 544/319; 544/321; 544/333; 544/334
[58] Field of Search ............... 544/295, 296, 320, 319, 544/123

[56] References Cited

U.S. PATENT DOCUMENTS

| | | | |
|---|---|---|---|
| 3,932,644 | 1/1976 | Durant et al. | 544/320 |
| 4,145,546 | 3/1979 | Brown et al. | 544/320 |
| 4,153,793 | 5/1979 | Durant et al. | 544/320 |
| 4,154,834 | 5/1979 | Brown et al. | 544/320 |
| 4,216,318 | 8/1980 | Brown et al. | 544/296 |
| 4,234,588 | 11/1980 | Brown et al. | 544/320 |

FOREIGN PATENT DOCUMENTS

| | | | |
|---|---|---|---|
| 24873 | 3/1981 | European Pat. Off. | 544/320 |
| 1582528 | 1/1981 | United Kingdom | 544/320 |

*Primary Examiner*—Mary C. Lee
*Attorney, Agent, or Firm*—William H. Edgerton; Richard D. Foggio; Alan D. Lourie

[57] ABSTRACT

A series of chemical reactions starting from the condensation of uracil with an acid stable heterocyclic aldehyde in an acid medium produces biologically active end products which are 2-heterocyclylmethylthioethylamino-5-heterocyclylmethyl-4-pyrimidinones. The new reactions and intermediates of this invention are particularly useful for preparing 2[2-(5-dimethylaminomethyl-2-furylmethylthio)-ethylamino]-5-(6-methyl-3-pyridylmethyl)-4-pyrimidinone and its salts. This compound is a potent H$_2$-antagonist with a long duration of activity.

17 Claims, No Drawings

CHEMICAL METHODS AND INTERMEDIATES FOR PREPARING SUBSTITUTED PYRIMIDINONES

This invention relates to novel chemical methods and intermediates for preparing pharmaceutically active chemical compounds such as those having histamine H$_2$-antagonist activity said compounds being substituted pyrimidinones.

Broadly the invention is based on a synthetic pathway starting with a condensation between a 2,4-disubstituted pyrimidine and certain heterocyclic aldehydes then proceeding through a number of novel chemical reactions and intermediates to prepare various 2-heterocyclylmethylthioethylamino- and 2-heterocyclyl-butylamino-5-heterocyclylmethyl-4-(1H)-pyrimidinones which comprise a series of compounds known in the art to have activity in inhibiting gastric activity. The prime step of this reaction sequence is the first of the synthetic sequence which involves the condensation of a basic heterocyclic aldehyde at the 5-position of a 2,4-disubstituted pyrimidine which has no substituent at the 5 or 6-positions.

1. Description of the Prior Art

In the prior art, 5-heterocyclylalkyl-2,4-disubstituted pyrimidines were prepared by reaction sequences which synthesize the pyrimidine ring, U.S. Pat. No. 4,154,834, U.K. patent application G.B. Pat. No. 2,030,979 or European patent application No. 3677. Reaction of uracil with formaldehyde to form 5-hydroxymethyluracil was reported by R. Brossner et al., Liebig's Ann. Chem. 692, 119 (1966) and R. E. Cline et al., J. Am. Chem. Soc. 81, 2521 (1959). Both references report that the hydroxymethylation of uracil proceeds best under alkaline rather than acid conditions. Also neither suggest any formation of bis by-products such as bisuracilmethane.

5-Benzylidene-6-(N-substituted amino) uracils were reported to result from the reaction of benzaldehydes with 3-methyl-6-(N-substituted amino)-uracil, O. Mori et al., J.C.S. Chem. Comm. 1978 764. Here, however, the 3-N-methyl substituent changes the tautomeric system of the uracil ring in counterdistinction to that of the uracil reactant in the key condensation step of the present invention. Also in Mori there is a 6-substituent present in the structure of the starting material.

2. Description of the Invention

The present reaction offers biologically active biheterocycle substituted pyrimidinones for example 2-ω-heterocyclylbutylamino- or 2-heterocyclylmethylthioethylamino-5-heterocyclylmethyl-4(1H)-pyrimidinones in good yield and at a low cost of chemical. Also the reaction sequence of this overall process is a technical advance over those in the literature for preparing the end products from an environmental viewpoint. For example no mercaptans need be generated and no potentially hazardous reagents need be used such as a nitroguanidine as used in the prior art process. Also fewer overall steps are involved in the synthetic sequence here claimed compared with that of the prior art. Certain steps of this process have a high chemical throughput.

It is surprising that this reaction sequence is successful as we found that aryl-bis(pyrimidin-5-yl)-methanes are undesirable byproducts when a 2,4-disubstituted pyrimidine was condensed with benzaldehyde or with benzaldehydes substituted with any substituent which is not of a high electronegative nature. For example, p-chloro, o, m or p-nitro, o,p-dichloro, p-trifluoromethyl and similar substituents activate benzaldehyde sufficiently to enable one to avoid formation of bis(-pyrimidinyl)methanes. Certain acid stable basic N-containing heterocyclic aldehydes, particularly the formyl pyridines such as nicotinaldehyde, also were found to give good yields of the desired condensation product having attachment at the 5-position of the pyrimidine ring with minimal formation of the bis byproducts. Other heterocyclic aldehydes such as thienylaldehyde or furfuraldehyde either do not react, decompose or give bis compounds.

The first step in this overall reaction sequence is therefore:

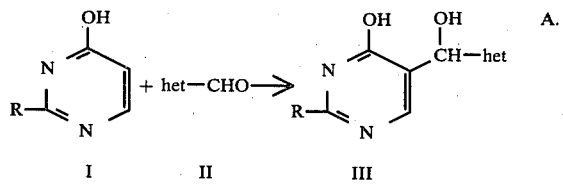

wherein:
R is hydroxy, mercapto or methylthio; and
het is an aromatic 5 or 6-membered heterocyclic ring which is stable under the acid reaction conditions described hereafter and which has at least one nitrogen ring member such as 2-pyridyl, 3-pyridyl, 4pyridyl, 2-thiazolyl, 2-oxazolyl, 2-imidazolyl, 2-pyrimidyl or 2-pyrazyl. A subgeneric group of this invention involves those compounds in which het is pyridyl optionally substituted with methyl such as 3-pyridyl or 6-methyl-3-pyridyl.

The term "het" more specifically includes 5 to 6 membered basic heterocyclic rings known to the art which have from 1-3 hetero members at least one of which must be nitrogen in the same ring as another hetero member if present. The other optional hetero ring members are oxygen or sulfur. C-substituents can be present on the rings such as methyl, ethyl, methoxy, ethoxy. The rings and the substituents must be either chemically inert under the reaction conditions of the individual chemical steps of this invention or be reactive in a controlled or selective manner as with the lower alkoxy substituents which may be split to hydroxy during the reactions outlined.

Of course the methyl, methoxy or other substituents including the attachment to the other part of the structure are by means of a C-ring member of the heterocyclic rings.

For good yields, the pyrimidine in whose structure R is hydroxy (that is, uracil) is used as starting material. Of course 2,4-dihydroxypyrimidine is one tautomeric form of uracil.

For preparing very active target compounds of the prior art, het is a pyridinyl or more specifically 6-methyl-3-pyridinyl.

The condensation reaction (A) is carried out by reacting the two starting materials usually in about equimolar quantities or with a slight excess of the aldehyde reagent. The medium may be any acid solvent in which the reactants are substantially soluble. Aqueous inorganic acid media are most useful for formyl pyridines. A pH range up to 5 is useful. Exemplary acids are the mineral acids such as phosphoric acid, sulfuric acid, 48% hydrobromic acid, 47% hydriodic acid and, especially, concentrated hydrochloric acid. Acetic acid is also used.

The reaction is run at temperatures from ambient to reflux until substantially complete. Using reflux temperature for from 4-10 hours in concentrated hydrochloric acid gives excellent yields.

It should be noted that other variations of reaction A will be apparent to those skilled in the art. For example, 2,4-dimethoxypyrimidine can be used in place of uracil in the reaction but the same product is isolated due to hydrolysis of the methoxy groups in the acid condensation medium.

The α-hydroxy products of Formula III are a part of this invention. These compounds may be isolated or may be used in situ for the following reaction:

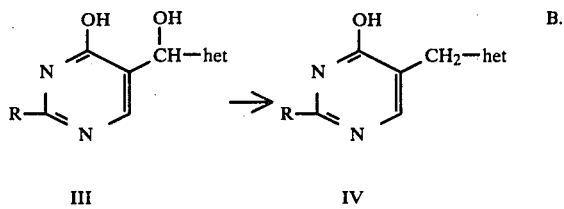

wherein R and het are as described above.

The α-hydroxy compounds of Formula III are then reacted using conditions known to the art for hydrogenolysis of benzylic or allylic alcohols such as catalytic hydrogenation using a transition metal catalyst preferably a palladium catalyst, 47% hydriodic acid-acetic anhydride-acetic acid, zinc-acetic acid or formic acid-triethylamine. The term "hydrogenolysis" is used to mean any chemical reaction which results in cleavage of the O-C bond at the α-position to result in a H-C bond either by a displacement or reduction reaction.

The hydriodic acid reaction is particularly important since it enables the operator to combine reactions A and B to give the important deshydroxy products (IV) in good yield. Here the pyrimidine and aldehyde starting materials are reacted in substantially equimolar quantities in a mixture of glacial acetic acid-acetic anhydride (1:1). An excess of 47% hydriodic acid is then added to displace the α-acetoxy group. After a brief reflux period, the mixture is treated with sodium bisulfite. The pH is then adjusted to obtain the desired product (IV).

The starting materials of reaction A, Formula I, in which R is mercapto and methylthio are usually converted to the uracil (IV, R=—OH) prior to further steps in the reaction sequence described hereafter and such a reaction is assumed in this disclosure and in these claims. For example either the 2-mercapto or 2-methylthio-4-hydroxypyrimidine when heated at reflux with 3-formylpyridine under the preferred hydriodic acid conditions detailed above gives the 5-heterocyclylmethyl-2,4-dihydroxypyrimidine (IV). Zinc-glacial acetic acid can also be used. Alternatively the discrete two step sequence of reactions A and B can be used.

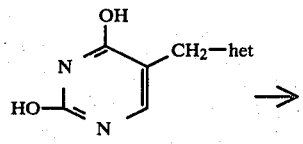

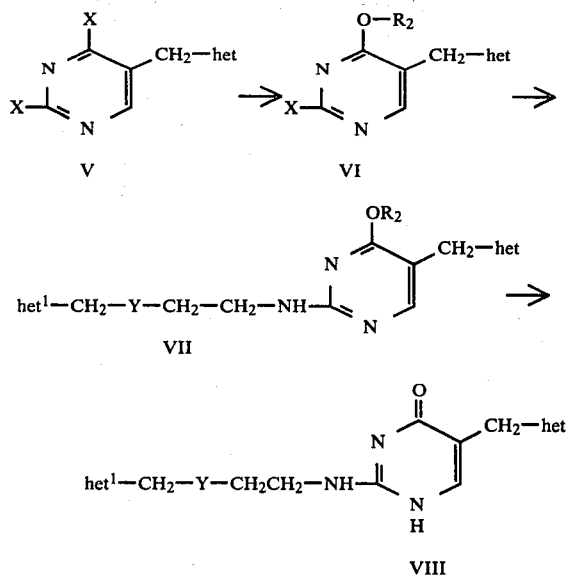

In reaction sequence C, het is as described above, Y is —CH$_2$— or —S—, X is bromo or preferably chloro and R$_2$ is lower alkyl of 1-5 carbons, benzyl, allyl, phenyl, 2-methoxyethyl or 2,2,2-trichloroethyl with benzyl or allyl being preferred (these groups are all included in the terms "alkoxy" or "alkoxide" used hereafter unless otherwise specified).

Het$^1$ is an optionally substituted aromatic 5 or 6 membered heterocyclic group having 1-3 heteroatoms which are nitrogen, sulfur or oxygen with the proviso that, when 2 of 3 heteroatoms are present, at least one is nitrogen.

Particular meanings of het$^1$ are a 2- or 4-imidazolyl group optionally substituted by lower alkyl, halogen, trifluoromethyl or hydroxymethyl, a 2-pyridyl group optionally substituted by one or more (which can be the same or different) lower alkyl, lower alkoxy, halogen, amino or hydroxy groups, a 2-thiazolyl group, a 2-guanidino-4-thiazolyl group, a 3-isothiazolyl group optionally substituted by chlorine or bromine, a 3-(1,2,5)thiadiazolyl group optionally substituted by chlorine or bromine, a 2-(5-amino-1,3,4-thiadiazolyl) group or a 2-furanyl or 2-thienyl group optionally substituted in the 5-position with a group R$_3$R$_4$N(CH$_2$)$_m$—; R$_3$ and R$_4$ are lower alkyl or together with the nitrogen atom to which they are attached form a pyrrolidino, piperidino or morpholino group; m is 1 to 4. A subgeneric group of compounds are those in which het$^1$ is 2-furanyl or 2-thienyl optionally substituted in the 5-position with R$_3$R$_4$N(CH$_2$)$_m$—; 4-imidazolyl optionally substituted in the 5-position with methyl or bromine; 2-pyridyl optionally substituted in the 3-position with lower alkyl, lower alkoxy, halogen, amino or hydroxy; 2-thiazolyl or 2-guanidino-4-thiazolyl. In this definition "lower alkyl" or "lower alkoxy" means alkyl or alkoxy groups of 1-3 carbons preferably methyl or methoxy respectively. Halogen is preferably chloro or bromo.

In reaction sequence C the 5-heterocyclylmethyl uracils of Formula IV are converted to the 2,4-dihalopyrimidines using a haloesterifying agent (that is, a known reagent which converts a reactive hydroxy group to a halo) such as an excess of thionyl chloride, oxalyl chloride, phosgene, thionyl bromide, phosphorus tribromide, phosphorus pentachloride and, especially, phosphorus oxychloride. Other such halogenating agents as known to the art may be also used.

The 5-heterocyclylmethyl-2,4-dihalopyrimidine (V) is then reacted with a substantially equimolar quantity of an alkali metal alkoxide, especially one containing an easily replaceable alkoxy group such as potassium or sodium benzylate or allylate, in an inert organic solvent such as an excess of the alcohol if it is one of the common solvents or another solvent such as tetrahydrofuran, dimethylsulfoxide, dimethylformamide or another alcohol. The mixture is allowed to react at temperatures selected from the range of about $-30°$ to reflux temperature until the reaction is complete. One skilled in the art will be aware that the alkali metal alkoxides will differ in reactivity.

The resulting 5-heterocyclylmethyl-2-halo-4-alkoxy pyrimidine (VI) is then condensed with a heterocyclylalkylamine (het$^1$—CH$_2$—Y—CH$_2$CH$_2$—NH$_2$), most conveniently by reacting a slight excess of the amine with the 2-halo-4-alkoxy compound (VI) in the presence of an excess of a base of low nucleophilicity such as a liquid tertiary amine. Since the nature of primary amine is not critical, any desired amine may be substituted for het$^1$—CH$_2$—Y—CH$_2$CH$_2$—NH$_2$. Excess triethylamine, tributylamine, pyridine, lutidine or N,N-dimethylaniline at 100°–120° is conveniently employed as solvent as well as the acid binding tertiary amine. Triethylamine is particularly useful for its reaction enhancing effect. Alternatively the heterocyclylalkylamine is reacted with (VI) in chemically inert inorganic solvents (an alcohol, for example, 1-hexanol or 2-octanol or a benzenoid solvent such as benzene or toluene) in the presence of an organic or inorganic base such as potassium carbonate, potassium hydroxide or 1,8-diazabicyclo[5.4.0]undec-7-ene with or without a phase transfer catalyst such as 18 crown 6 or others described in Aldrichemica Acta 8 35 (1976) within the temperature range of from 60°–185° preferably 100°–160°. In some cases an excess of the heterocyclic amine reactant can act as an acid binding agent with no added solvent. A convenient reaction is obtained by heating the reactants in triethylamine as solvent from 75°–120° until reactio is complete. The 4-dealkylation and 2-condensation steps may be inverted in order if the operator so desires however the sequence as described is preferred.

As an alternative route, the displaceable 2-halo group at the 2-position may be replaced by a second displaceable group which is in turn reacted with the chosen heterocyle primary amine preferably after hydrogenolysis of the 4-alkoxy group. One such second group is a lower alkoxy of 1–5 carbons such as methoxy or ethoxy. Another is a lower alkylthio or benzylthio but thio containing groups are less desirable because of a lower capability of being displaced or from environmental considerations.

Under certain circumstances when a less reactive displaceable group is desired at position 2 of the pyrimidine the alkoxy may be used rather than a chloro or bromo substituent.

Among the 2-alkoxypyrimidinones used in this fashion are those of the formula:

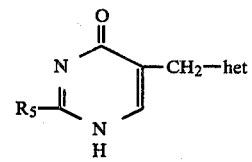

in which het is as described above and R$_5$ is alkoxy of 1–5 carbons such as methoxy, ethoxy or butoxy.

Preferred 4-alkoxy groups in the pyrimidine VI are those which are readily removed in the presence of the 2-alkoxy substituents especially 4-benzyloxy which is easily removed by catalytic hydrogenation.

The 4-alkoxy compound (VII) is conveniently dealkylated by reactions as described hereafter to regenerate the 4-(1H)-pyrimidinone moiety of the desired end product (VIII). For example, if a relatively stable ether group is present such as in lower alkoxy containing compounds, heating at reflux in hydriodic or hydrobromic acid as well as treatment with boron tribromide in the cold is effective. If a more easily displaced alkoxy group is present, such as the preferred benzyloxy or allyloxy, alcoholic acid treatment is applicable for example heating at reflux in 10% hydrochloric acid in methanol, ethanol or isopropanol to give the desired product having histamine H$_2$-antagonist activity (VIII). Under certain conditions which one skilled in the art will recognize certain substituents on the heterocyclic rings such as lower alkoxy group will also be split as well such as during treatment with hydriodic or hydrobromic acid.

In summary the term dealkylation applied to the 4-alkoxy compound can mean a hydrolysis, hydrogenolysis or any convenient ether splitting reaction known to the art depending on the reactivity of the 4-alkoxy substituent.

It will also be apparent to one skilled in the art that other desirable structural modifications may be inserted into the essential steps of the reaction sequence described above. For example when het$^1$ is a 2-furyl moiety a dimethylaminomethyl group is optionally inserted into the 5-position of the furyl ring prior to dealkylation of the 4-alkoxy pyrimidinone intermediate (VII) by treatment with bis(dimethylamino)methane or with formaldehydedimethylamine under standard Mannich reaction conditions. The dealkylation step is then run to prepare the desired final product as described above. This stepwise procedure is important because of the lability of the furan ring to the conditions of the dealkylation reaction. An unexpected stabilizing effect to the conditions of the reaction is imparted to the furyl ring by the presence of the Mannich moiety. As noted hereabove inversion of the steps described is also useful to prepare individual end products.

A group of key intermediates of this invention is of the formula:

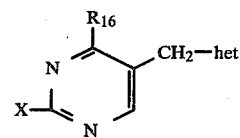

IX in which het is described as above, R$_6$ is chloro, bromo, lower alkoxy of 1–5 carbons, benzyloxy, allyloxy, phenoxy, 2-methoxyethoxy or 2,2,2-trichloroethoxy and X is bromo, chloro or, when R₆ is other than bromo or chloro, lower alkoxy of 1–5 carbons especially methoxy or ethoxy. Of these compounds a subgeneric group of prime utility are those in which X is chloro, R₆ is chloro, benzyloxy or allyloxy and het is 3-pyridinyl or 6-methyl-3-pyridinyl. Species of this group include 2,4-dichloro-5-[(6-methyl-3-pyridinyl)-methyl]-pyrimidine, 4-benzyloxy-2-chloro-5-[(6-methyl-3-pyridinyl)methyl]pyrimidine, 4-benzyloxy-2-methoxy-5-[(6-methyl-3-pyridinyl)methyl]pyrimidine or 4-allyloxy-2-chloro-5-[(6-methyl-3-pyridinyl)methyl]pyrimidine.

Also included in this invention are a number of other novel intermediates prepared in this new reaction sequence such as those of the formula:

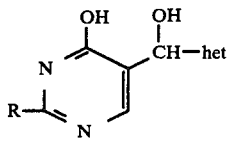

III in which R and het are as defined above. A subgeneric group of these compounds of particular utility is the compounds of Formula III in which R is hydroxy, het is 3-pyridinyl or 6-methyl-3-pyridinyl. A key compound is 5-[(6-methyl-3-pyridinyl)-hydroxymethyl]-2,4-(1H,3H)-pyrimidinedione.

Another group of intermediates of this invention is that of the formula:

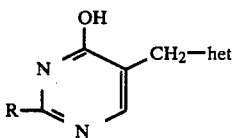

IV in which R and het are as defined above. Once again a subgeneric group of these compounds of particular utility are the compounds in which R is hydroxy, het is 3-pyridinyl or 6-methyl-3-pyridinyl. A key compound is 5-[(6-methyl-3-pyridinyl]methyl-2,4-(1H,3H)-pyrimidinedione.

Certain compounds related to these are generically disclosed in U.S. Pat. No. 4,154,834 in which R is mercapto or chloro, however, the synthetic methods of that reference are not applicable to the compounds of Formula IV.

A last group of intermediates of this invention is:

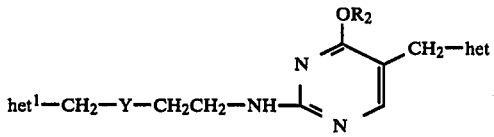

in which R₂, Y, het and het¹ are as described above. A subgeneric group of these compounds are the compounds in which het¹ is 2-furyl or 5-dimethylaminomethyl-2-furyl, Y is —S— and het is pyridinyl. Species of particular utility are those of the subgeneric group in which R² is benzyl or allyl and het is 6-methyl-3-pyridinyl.

It will be understood that, while the bases of the novel intermediates described above are of prime use, their acid addition salts with acids useful in chemical synthetic procedures may be alternatively prepared. Whenever one or more basic center is present in the structures, salts are prepared with hydrochloric, hydrobromic, sulfuric, phosphoric, oxalic, formic, ethanedisulfonic, methanesulfonic acids. These are prepared by standard reactions such as in alcoholic solution with an excess of acid. The compounds of Formula III are intractable solids in base form which form stable salts only with difficulty.

The following examples are designed solely to illustrate the practice of this invention and its possible variations but are not intended to limit the scope of this invention. The abbreviations in the Examples are as follows: IR, infrared spectrum; NMR, nuclear magnetic resonance; MS, mass spectrum; tlc, thin layer chromatography; CDCl₃, deuterochloroform.

EXAMPLE 1

Uracil (224 g, 2 mol) was added to 1.4 L of conc. hydrochloric acid and the slurry was warmed to ~60°. To this warm suspension was added 2-methyl-5-formylpyridine (270 g, 2.2 mol). The suspension was then heated to reflux for 8 hours and allowed to cool to room temperature. The cooled solution was filtered and the residue discarded. The filtrate was basified to pH 8–8.5 with 10 N sodium hydroxide solution and the solid product precipitated. The product was isolated by vacuum filtration and washed with 300 ml of acetone. The product, 5-[(6-methyl-3-pyridinyl)hydroxymethyl]-2,4-(1H,3H)-pyrimidinedione, was dried at 60° to yield 325 g (69.7%); m.p. 312°–316° (dec.).

Anal. Calcd. for $C_{11}H_{11}N_3O_3$: C, 56.65; H, 4.75; N, 18.02. Found: C, 57.03; H, 4.88; N, 18.00.

The α-hydroxy compound (1 kg, 4.3 mol) was suspended in 16 L of acetic acid and 5% palladium-on-carbon catalyst (50% wet, 0.382 g) was added to the mixture. The reaction mixture was charged into a 5 L autoclave and hydrogenated with 40 psi (2.068 KPS) at 60° for 6 hours. Then the reaction solution was filtered and concentrated to an oil (1.5 L). The oil was dissolved in 3 L of water and the pH of the solution adjusted to 7.5 with 50% caustic without cooling. The warm alkaline solution was then cooled to 15° and filtered. The product was washed with water and dried in a steam cabinet to yield 762 g (82%); 5-[(6-methyl-3-pyridinyl)methyl]-2,4-(1H,3H-pyrimidinedione. Other noble metal catalysts are also suitable.

The dehydroxylated compound (700 g, 3.23 mol) and phosphorus oxychloride (2.1 L) were mixed and heated to gentle reflux. After 3 hours, the dark brown solution was cooled to room temperature. The excess phosphorus oxychloride was removed under vacuum leaving a solid mass. The solid was heated on a steam bath and the resulting liquid slurried with chloroform (2.5 L). The slurry was slowly poured into ice-water (2.5 L) keeping the temperature below 17°. The quenched mixture was basified to pH 8 with 20% sodium hydroxide solution keeping the temperature below 25°. The organic layer separated was removed and the water layer was extracted with 2×2 liters of chloroform. The combined chloroform extracts were dried over sodium sulfate and the solvent removed under vacuum leaving a dark brown solid 2,4-dichloro-5-[(6-methyl-3-pyridinyl)methyl]pyrimidine weighing 778.76 g (95%): ¹H NMR(CDCl₃), 2.65 (3H, s), 4.15 (2H, s), 6.6 (1H, s), 6.9 (1H, d), 7 (1H, dd), 7.8 (1H, s).

Anal. Calcd. for $C_{11}H_9Cl_2N_3$: C, 51.99; H, 3.57; N, 16.54; Cl, 27.90. Found: C, 51.91; H, 3.58; N, 16.71; Cl, 27.07.

Phosphorus tribromide in pyridine is also used to form the 2,4-dibromo congener which is then substituted in the following reaction sequence.

Sodium metal (0.23 g, 0.01 gram-atom) was dissolved in 10 ml of dry methanol. The methanolic sodium methoxide solution was added dropwise into solution of the 2,4-dichloro compound (2.53 g, 0.01 mol) in methanol (15 ml) at 5°. The reaction was stirred overnight at room temperature and concentrated to a thick oil which was dissolved in 30 ml of methylene chloride. The methylene chloride solution was filtered and evaporated to yield 2.3 g (mp 86°–88°, 93%) of the product: 2-chloro-4-methoxy-5-[(6-methyl-3-pyridinyl)methyl]-pyrimidine.

Anal. Calcd. for $C_{12}H_{12}ClN_3O$: C, 57.72; H, 4.84; N, 16.83. Found: C, 57.74; H, 4.76; N, 16.90.

2-Chloro-4-methoxy-5-[(6-methyl-3-pyridinyl)-methyl]pyrimidine (2.5 g, 0.01 mol) and α-furylmethylthioethylamine (3.2 g, 0.02 mol) were heated in the presence of potassium carbonate (2.78 g) at 100° for 4 hours. The reaction was cooled to room temperature and was dissolved in ethyl acetate (20 ml). The organic solution was extracted with water (2×20 ml) and concentrated to an oil which was purified using high pressure liquid chromatography (silica gel; 5% methanol in methylene chloride). The product obtained was 2.7 g of an oil (0.014 mol, 72) 2-[[2-[(2-furylmethyl)thio]ethyl]-amino]-4-methoxy-5-[(6-methyl-3-pyridinyl)methyl]-pyrimidine; MS(m/e) 370. $^1$H NMR(CDCl$_3$) δ2.48 (3H, s), 2.7 (2H, m), 3.5 (2H, m), 3.7 (2H, s), 3.8 (3H, s), 6.65 (2H, m), 6.9 (1H, d), 7.2 (2H, d), 7.35 (1H, m), 7.8 (1H, s), 8.3 (1H, s).

2-[[2-[(2-Furylmethyl)thio]ethyl]amino]-4-methoxy-5-[(6-methyl-3-pyridinyl)methyl]pyrimidine (0.2 g., 0.05 mmol) was dissolved in acetic acid (2 ml). Bis(dimethylamino)methane (0.15 g, 0.15 mmol) was added to the above solution. The solution was stirred overnight, then concentrated to an oil which was taken up in water (2 ml). The aqueous solution was basified to pH 8–9 with potassium carbonate. A gummy material that separated from the aqueous solution was extracted with ethyl acetate (2×5 ml). The organic extract was dried and concentrated to 0.2 g of an oil (0.045 ml., 90%): MS(m/e) 427, 2-[[2-[[[5-[(dimethylamino)methyl]-2-furyl]methyl]-thio]ethyl]amino]-4-methoxy-5-[(6-methyl-3-pyridinyl)-methyl]pyrimidine.

2-[[2-[[[5-[(Dimethylamino)methyl]-2-furanyl]-methyl]thio]ethyl]amino]-4-methoxy-5-[(6-methyl-3-pyridinyl)methyl]pyrimidine (0.1 g, 0.023 mmol) was dissolved in glacial acetic acid (2 ml). Hydriodic acid (48%, 1 ml) and red phosphorus (0.5 g) were added to the above solution. The mixture was heated to 105°. After one hour, the reaction was cooled and concentrated to an oil which was dissolved in 5 ml of water. The aqueous solution was basified and extracted with ethyl acetate (2×5 ml). The organic phase was dried and concentrated to give 0.05 g (0.012 mol, 50%) of product: MS(m/e) 414 (M+H), 2-[[2-[[[5-[(dimethylamino)methyl]-2-furyl]methyl]thio]ethyl]amino]-5-[(6-methyl-3-pyridinyl)methyl]-4-(1H-pyrimidinone. The melting point of the trihydrochloride salt is 224°–227° formed by reacting the base with an excess of ethanolic hydrogen chloride.

EXAMPLE 2

To formic acid (95–97%, 465.75 g, 10.125 mol) in a two liter, round bottom flask fitted with a mechanical stirrer, Dean Stark-trap, reflux condenser and thermometer was added triethylamine (390 g, 3.866 mol). 5-[(6-Methyl-3-pyridinyl)hydroxymethyl]-2,4-(1H,3H)-pyrimidinedione (400 g, 1.716 mol) was added and the mixture heated at 160° for 20 hrs. The cooled reaction mixture was diluted with 500 ml water and the pH adjusted to 8–9 with ammonium hydroxide. After filtration and drying 318 g (85.8%) of 5-[(6-methyl-3-pyridinyl)methyl]-2,4-(1H,3H)-pyrimidinedione was obtained: m.p. 256°–260°.

Anal. Calcd. for $C_{11}H_{11}N_3O_2$: C, 60.82; H, 5.10; N, 19.34. Found: C, 60.70; H, 4.91; N, 19.53.

EXAMPLE 3

Uracil (5 g, 0.045 mol) and 2-methyl-5-formylpyridine (7.09 g, 0.045 mol) were dissolved in a mixture of acetic acid (20 ml) and acetic anhydride (20 ml). Hydriodic acid (47%, 25 ml, 0.138 mol) was added dropwise over ten minutes. The solution was allowed to cool for 15 minutes and then heated to reflux for 5 hours. The reaction mixture was cooled and sodium bisulfite (21.2 g) added. The brown solution turned pale yellow and the solution was adjusted to pH 7.2 with 40% sodium hydroxide solution. A white precipitate formed and was collected by filtration. The product was dried in vacuum at 60°: 5.88 g (57.8%) which is identical to that obtained in Example 1 by the first two chemical steps.

This material was reacted with phosphorus oxychloride as described in Example 1 to form the 2,4-dichloro product. Benzyl alcohol (123 g, 1.14 mol) and sodium isopropoxide (46.7 g, 0.57 mol) were heated in 250 ml of tetrahydrofuran to 125° for 0.5 hours. The cooled solution was then added dropwise to 2,4-dichloro-5-[(6-methyl-3-pyridinyl)methyl]pyrimidine (132.0 g, 0.52 mol) in 400 ml of dimethylformamide at −30° over 1 hour. High pressure liquid chromatography (7:3 methanol: 0.01 M monosodium phosphate, reverse phase column, 254 Mu, 1 ml/min) showed the reaction to be complete after 1.5 hours. The reaction mixture was then poured into 2.5 L of ice-water and allowed to stand overnight. The solid that formed was removed by filtration to yield 157.8 g of solid product, 2-chloro-4-benzyloxy-5-[(6-methyl-3-pyridinyl-methyl]pyrimidine, (0.485 mol, 93%) containing 2.2% (using an external standard) of the everse addition isomer: m.p. (crude) 80°, ref (95.5°–96.5°); IR(neat) 1550, 1400, 1320, 1230, 1000, 940, 740, 690; $^1$H NMR(CDCl$_3$), δ2.5 (s, 3H, py-r—CH$_3$), 3.8 (s, 2H, —CH$_2$-pyridinyl), 5.4 (s, 2H, —O—CH$_2$-Ph), 6.9–7.4 (m, 7H, Ar), 8.1 (s, 1H, 6-pyrimidinyl), 8.35 (s, 1H, 6-pyridinyl).

Anal. Calcd. for $C_{18}H_{16}ClN_3O$: C, 66.36; H, 4.95; N, 12.90. Found: C, 66.12; H, 4.89; N, 12.85.

2-Chloro-4-benzyloxy-5-[(6-methyl-3-pyridinyl)-methyl]pyrimidine (9.18 g, 0.0282 mol) and α-furylmethylthioethylamine (5.43 g, 0.0346 mol) were heated for 16 hours at 110° with 3 equivalents (10.48 g) of triethylamine as solvent. Additional (3 g) triethylamine was added during the course of the reaction to dissolve precipitated salts. The reaction mixture was then dissolved in water and extracted with ether. The ether layer was extracted several times with saturated ammonium chloride solution. The ether layer was extracted with 10% hydrochloric acid and the organic layer was discarded. The aqueous layer was basified to pH 6.0–6.5 using 10% sodium hydroxide and extracted with ether. During the last extraction a polar impurity remained in the aqueous layer. The ether layer was dried and concentrated to yield 12.0 g (0.2687 mol, 87% crude) of the desired product: 2-[[2-[(2-furylmethyl)thio]ethyl]amino]-4-benzyloxy-5-[(6-methyl-3-pyridinyl)methyl]-pyrimidine. M.P. of the base was 66°–67°, the oxalate salt, 91°–94°.

Anal. Calcd. for $C_{25}H_{26}N_4O_2S$: C, 67.24; H, 5.87; N, 12.55. Found: C, 67.15; H, 5.78; N, 12.63.

The condensed product (12.0 g, 0.02687 mol) was dissolved in 50 ml of acetic acid. Bis(dimethylamino)methane (18 g, 0.176 mol) was added and the solution was stirred at room temperature 16 hours. At the end of this time, the solvent was removed and the residue was dissolved in 10% hydrochloric acid (100 ml) and basified with potassium carbonate solution. The aqueous solution was then extracted with ether several times. The combined and dried ether extracts were concentrated to dryness to yield 14.5 g of an oil: 2-[[2-[[[5-[(dimethylamino)methyl]-2-furyl]methyl]thio]ethyl]amino]-4-benzyloxy-5-[(6-methyl-3-pyridinyl)methyl]pyrimidine. IR(neat) 3300(N-H), 1000(—O—CH$_2$) cm$^{-1}$; $^1$H NMR(CDCl$_3$) δ2.25 (s, 6H), 2.5 (s, 3H), 2.6–3.4 (m, 4H), 3.4 (m, 2H), 3.75 (m, 2H), 5.35 (s, 2H), 6.1 (s, 2H), 6.9–7.4 (m, 7H), 7.9 (d, 1H), 8.4 (d, 1H).

Anal. Calcd. for $C_{28}N_{33}N_5O_2S$ $H_2O$: C, 64.47; H, 6.71; N, 13.42. Found: C, 64.40; H, 6.71; N, 13.16.

The Mannich product is also prepared by heating the furyl containing compound with one equivalent of dimethylamine and paraformaldehyde in isopropanol at reflux for 16 hours.

The Mannich product [2.1 g (crude), 0.0417 mol] was dissolved in 30 ml of isopropanol and 15 ml of 10% hydrochloric was added. The solution was heated under reflux (85°) for 6 hours and then was allowed to cool. The solvent was removed and the residue obtained was washed with ether, then basified with 10% sodium hydroxide solution and extracted with chloroform. The combined and dried organic extracts were concentrated to yield an oil that crystallized from acetone/ether: 1.5 g (0.0363 mol, 87%) of 2-[[2-[[[5-(dimethylamino)methyl]-2-furyl]methyl]thio]ethyl]amino]-5-[(6-methyl-3-pyridinyl)methyl]-4-(1H)pyrimidinone; tlc and MS(m/e) 414 (M+H) were satisfactory; m.p. 112°.

EXAMPLE 4

To a stirred solution of 8.1 g (32 mmol) of 2,4-dichloro-5-[(6-methyl-3-pyridinyl)methyl]pyrimidine prepared as in Example 1 in 200 ml of ethanol at 10° was added dropwise over 1 hour a solution of 0.8 g (35 mg-atom) of sodium metal in 100 ml of ethanol. The resulting mixture was stirred for 18 hours at room temperature, concentrated, and the resulting oil dissolved in 100 ml of ethyl acetate. The resulting solution was washed with water, dried over sodium sulfate, filtered and concentrated to give 7.6 g (0.0288 mmol, 90%) of 2-chloro-4-ethoxy-5-[(6-methyl-3-pyridinyl)methyl]-pyrimidine; MS(FD)m/e 263 parent ion.

This compound (1 g in each run) is reacted with an excess of 4-(3-methoxy-2-pyridinyl)butylamine, 2-[(5-methyl-4-imidazolylmethyl)thio]ethylamine or 2-[(2-thiazolylmethyl)thio]ethylamine in the last two reactions of Example 1 to give 4-ethoxy-5-[(6-methyl-3-pyridinyl)methyl]-2-[[4-(3-methoxy-2-pyridinyl)butyl]amino]-pyrimidine, 4-ethoxy-5-[(6-methyl-3-pyridinyl)methyl]-2-[[2-[(5-methyl-4-imidazolylmethyl)thio]ethyl]amino]pyrimidine and 4-ethoxy-2-[[2-[(2-thiazolylmethyl)thio]ethyl]amino]-5-[(6-methyl-3-pyridinyl)methyl]pyrimidine and their corresponding 4-(1H)-pyrimidinone end products after splitting the ether using boron tribromide in ethylene chloride in the cold.

EXAMPLE 5

Phenol (1.1 g, 0.0118 mol) was dissolved in 50 ml of tetrahydrofuran and 0.284 g (0.0118 mol) of sodium hydride was added bulkwise. The suspension was stirred at room temperature for 0.5 hours then was added dropwise to a cooled (0°) tetrahydrofuran solution of the 2,4-dichloro compound of Example 1 (3.0 g, 0.0118 mol). The reaction mixture was allowed to stir for 3 hours at this temperature then was quenched with 10% hydrochloric acid. The aqueous layer was washed with ether then basified with 10% sodium hydroxide solution and extracted with ether. The ether extract was dried and concentrated to yield 3.8 g of an oily solid; $^1$H NMR(CDCl$_3$) δ2.5 (s, 3H), 3.9 (s, 2H), 6.9–7.5 (m, 7H), 8.2 (s, 1H), 8.4 (s, 1H); 2-chloro-4-phenoxy-5-[(6-methyl-3-pyridinyl)methyl]pyrimidine.

Anal. Calcd. for $C_{17}H_{14}ClN_3O$: C, 65.50; H, 4.53; N, 13.48. Found: C, 65.43; H, 4.25; N, 13.40.

This compound (2 g) is condensed with an excess of 2-[(2-(1,3,4)-thiadiazolylmethyl)thio]ethylamine gives 2-[[2-[[(1,3,4)-thiadiazolylmethyl]thio]ethyl]amino]-5-[(6-methyl-3-pyridinyl)methyl]-4-phenoxypyrimidine and its 4-(1H)-pyrimidinone after hydrolysis of the phenoxy group as described above.

EXAMPLE 6

To a stirred solution of 44.6 g (0.176 mol) of 2,4-dichloro-5-[(6-methyl-3-pyridinyl)methyl]pyrimidine from Example 1 in 300 ml of 2-methoxyethanol at 0°–5° was added dropwise over 2 hours a solution of 4.25 g (0.177 g-atom) of sodium metal in 250 ml of 2-methoxyethanol. The solution was stirred for 30 minutes at 5°, concentrated and the resulting oil dissolved in 500 ml of ethyl acetate. The solution was washed with water, dried over sodium sulfate, filtered and concentrated to give 40.4 g (0.137 mol, 78%) of 2-chloro-4-(2-methoxyethoxy)-5-[(6-methyl-3-pyridinyl)methyl]pyrimidine: m.p. 50°–52°.

Anal. Calcd. for $C_{14}H_{16}ClN_3O_2$: C, 57.24; H, 5.49; N, 14.30. Found: C, 56.95; H, 5.53; N, 14.49.

2-Chloro-4-(2-methoxyethoxy)-5-[2-(6-methyl-3-pyridinyl)methyl]pyrimidine (24.8 g, 0.084 mol) and 27.2 g (0.173 mol) of 2-[(2-furylmethyl)thio]ethylamine were heated under nitrogen at 110° for 3 hours. The mixture was then cooled and treated with 100 ml of water and extracted with several portions of methylene chloride. The organic extracts were combined, washed with water, washed with 20% aqueous ammonium chloride, then dried over sodium sulfate. The solvent was then removed under vacuum to yield 30.0 g (86%) of 2-[[2-[(2-furylmethyl)thio]-ethyl]amino]-4-(2-methoxyethoxy)-5-[(6-methyl-3-pyridinyl)methyl]-pyrimidine as an oil: IR (KBr) 2850, 1605, 1580, 1525 cm$^{-1}$; $^1$H NMR(CDCl$_3$) δ2.48 (s, 3H), 2.70 (t, 2H), 3.35 (s, 3H), 3.60 (m, 4H), 3.70 (s, 2H), 4.38 (t, 2H), 6.10 (d, 1H), 6.24 (d, 1H), 7.0 (d, 1H), 7.35 (m, 2H), 7.85 (s, 1H), 8.37 (d, 1H); MS(FD)m/e 414 (M+H).

2-[[2-[(2-Furylmethyl)thio]ethyl]amino]-4-(2-methoxyethoxy)-5-[(6-methyl-3-pyridinyl)methyl]pyrimidine (34.2 g, 0.083 mol) and 25.3 g (0.25 mol) of bis(dimethylamino)methane were dissolved in 200 ml of glacial acetic acid and stirred at room temperature for 20 hours. The resulting solution was concentrated, basified to pH 8.0 with 10% aqueous potassium carbonate and extracted with several portions of methylene chloride. The combined extracts were washed with a saturated sodium chloride solution, dried over sodium sulfate, filtered and concentrated to give 36.3 g (0.77 mol, 93%) of crude oily 2-[[2-[[[2-[5-(dimethylamino)methyl]-2-furyl]methyl]thio]ethyl]amino]-4-(2-methoxyethoxy)-5-[(6-methyl-3-pyridinyl)methyl]pyrimidine. IR(neat) 2850, 1605, 1570, 1555 cm$^{-1}$; $^1$H NMR(CDCl$_3$) δ2.25 (s, 6H), 2.5 (s, 3H), 2.80 (m, 4H), 3.35 (s, 3H), 3.42 (s, 2H), 3.70 (overlapping singlets, 6H), 4.30 (m, 4H), 6.10 (bs, 2H), 7.0 (d, 1H), 7.40 (d, 1H), 7.85 (d, 1H), 8.35 (m, 1H).

This oily material (10 g) is hydrolyzed as described in Example 3 to give the desired 4-(1H)-pyrimidinone product.

EXAMPLE 7

A solution of 1.38 g (0.06 g-atom) of sodium metal in 25 ml of isopropanol was heated to reflux until complete dissolution of the metal. The alkoxide solution was cooled to −10° and treated dropwise with a solution of 15.0 g (60 mmol) of 2,4-dichloro-5-[(6-methyl-3-pyridinyl)methyl]pyrimidine prepared as in Example 1 in 60 ml of isopropanol. The resulting mixture was allowed to warm to room temperature over 18 hours and was then concentrated. The resulting oil was dissolved in ethyl acetate, filtered, washed with water, dried over magnesium sulfate, filtered, concentrated and dried under vacuum to give 14.5 g (0.052 mol, 87%) of 2-chloro-4-isopropoxy-5-[(6-methyl-3-pyridinyl)methyl]-pyrimidine. Recrystallization from ethyl acetate and petroleum ether gave yellow crystals: m.p. 38°–42°.

Anal. Calcd. for C$_{14}$N$_{16}$ClN$_3$O: C, 60.54; H, 5.81; N, 15.13. Found C, 60.55; H, 5.57; N, 15.14.

A mixture of 65.0 g (0.23 mol) of 2-chloro-4-isopropoxy-5-[6-methyl-3-pyridinyl)methyl]pyrimidine and 44.1 g (0.28 mol) of 2-[(2-furylmethyl)thio)ethylamine in 200 ml of triethylamine was heated under reflux for 48 hours. The solvent was removed and the residue dissolved in ethyl acetate then washed once with water and several times with 20% aqueous ammonium chloride. The organic solution was dried over sodium sulfate, filtered then concentrated to give 85.8 g (92%) of crude 2-[[2-[(2-furylmethyl)thio]ethyl]amino]-4-isopropoxy-5-[(6-methyl-3-pyridinyl)methyl]pyrimidine.

This crude material (67.3 g, 0.169 mol) and 68.9 g (0.68 mol) of bis(dimethylamino)methane was dissolved in 500 ml of glacial acetic acid and stirred at room temperature for 18 hours. The solvent was removed and the residue treated with excess 10% sodium hydroxide solution then extracted with ethyl acetate. The organic layer was dried over sodium sulfate, filtered and concentrated to give 62 g (63%) of crude 2-[[2-[[[5-[(dimethylamino)-methyl]-2-furyl]methyl]thio]ethyl]amino]-4-isopropoxy-5-[(6-methyl-3-pyridinyl)methyl]pyrimidine. Chromatography on silica gel (0.2 ml:0.5 ml:9.3 ml/NH$_4$OH, CH$_3$OH, EtOAc) gave pure product: IR (neat) 2950, 2925, 1610, 1580 cm$^{-1}$; $^1$M NMR (CDCl$_3$) δ8.25 (d, 1 M), 7.80 (S, 1 M), 7.35 (dd, 1 M), 6.95 (d, 1H), 5.0 (S, 2H), 4.25 (m, 1H), 3.70 (S, 2H), 3.60 (S, 2H), 3.50 (m, 2H), 2.70 (m, 2H), 2.45 (S, 3H), 2.10 (S, 6H), 1.20 (d, 6M); MS (m/e) 455.

This compound is hydrolyzed by the procedure of Example 3 to give the 4-(1H)-pyrimidinone.

EXAMPLE 8

To a stirred solution of 118.0 g (0.465 mol) of 2,4-dichloro-5-[(6-methyl-3-pyridinyl)methyl]pyrimidine from Example 1 in 200 ml of allyl alcohol and 300 ml of tetrahydrofuran at 0°–5° was added dropwise over 2 hours a solution of the sodium salt of allyl alcohol [generated from 22.4 g (0.465) of sodium hydride (50% oil dispersion) and 200 ml of allyl alcohol]. The mixture was stirred 30 minutes at 5°, warmed to room temperature and concentrated. The resulting oil was dissolved in 1 L of methylene chloride, washed with water, dried over sodium sulfate, filtered, and concentrated to give 112.0 g (0.0409 mol, 88%) of 2-chloro-4-allyloxy-5-[(6-methyl-3-pyridinyl)methyl]pyrimidine as crystals: IR(-Nujol) 2850, 2650, 1655, 1580, 1560 cm$^{-1}$; $^1$H NMR(D$_6$-DMSO/CDCl$_3$) δ2.45 (s, 3H), 3.85 (s, 2H), 4.90 (dd, 2H), 5.25 (dd, 1H), 5.34 (dd, 1H), 6.00 (m, 1H), 7.10 (d, 1H), 7.48 (dd, 1H), 8.30 (s, 1H), 8.35 (d, 1H).

2-Chloro-4-(2-allyloxy)-5-[2-(6-methyl-3-pyridinyl)-methyl]pyrimidine (44.0 g, 0.16 mol) and 50.1 g (0.32 mol) of 2-[(2-furylmethyl)thio]ethylamine were heated under nitrogen at 110° for 4 hours. The mixture was cooled, dissolved in 250 ml of methylene chloride, washed with water, 20% aqueous ammonium chloride, then dried over sodium sulfate. The solvent was removed under vacuum to yield 61.4 g (97%) of 2-[[2-[(2-furylmethyl)thio]ethyl]-amino]-4-(2-allyloxy)-5-[(6-methyl-3-pyridinyl)methyl]-pyrimidine as white needles, m.p. 47°–48°, IR (KBr). 3100, 1615, 1525 cm$^{-1}$; $^1$H NMR (CDCl$_3$/D$_6$DMSO) δ8.25 (d, 1H), 2.80 (S, 1H), 7.35 (m, 2H), 7.00 (d, 1H), 6.25 (d, 1H), 6.10 (d, 1H), 5.80 (m, 1H), 5.25 (m, 2H), 4.75 (dd, 2H), 3.70 (S, 2M), 3.60 (S, 2H), 3.50 (m, 2H), 2.90 (S, 3H), 2.90 (S, 3H), 2.70 (m, 2H), 2.50 (S, 3H); MS (m/e) 396.

Anal. Calcd. for C$_{21}$H$_{24}$N$_4$O$_2$S: C, 63.61; H, 6.10; N, 14.13. Found: C, 63.36; H, 6.11; N, 13.91.

2-[[2-[(2-Furylmethyl)thio]ethyl]amino]-4-allyoxy-5-[(6-methyl-3-pyridinyl)methyl]pyrimidine (16.0 g, 0.04 mol) and 12.4 g (0.12 mol) of bis(dimethylamino)methane in 100 ml of glacial acetic acid was stirred at room temperature for 22 hours. The solution was cooled to 10° and neutralized (pH>8.0) with 10 N sodium hydroxide then extracted with ethyl acetate. The organic solution was washed with brine then dried over sodium sulfate, filtered and concentrated to yield 16.1 g (89%) of crude product. Chromatography over silica gel gave white crystals of the Mannich compound, m.p. 58°–60°: IR (KBr) 2950, 1615, 1580, 1540 cm$^{-1}$; $^1$H NMR (D$_6$-DMSO/CDCl$_3$) δ8.38 (d, 1H), 7.85 (S, 1H), 7.35 (dd, 1H), 7.0 (d, 1H), 5.8–6.5 (m, 3H), 5.20 (dd, 2H), 4.70 (dd, 2H), 3.70 (S, 2H), 3.60 (S, 2H), 3.50 (m, 2H), 3.25 (S, 3H), 2.75 (m, 2H), 2.50 (S, 2H), 2.10 (S, 3H), 1.90(S, 3H); MS (m/e) 453.

Anal. Calcd. for C$_{24}$H$_{31}$N$_5$O$_2$S: C, 63.55; H, 6.89; N, 15.44. Found: C, 63.90; H, 6.97; N, 15.12.

This compound is hydrolyzed by the procedure of Example 3 to give the 4(1H)-pyrimidinone.

EXAMPLE 9

A mixture of 10.0 g (0.07 mol) of 2-methylthio-4-hydroxypyrimidine and 12.4 g (0.079 mol) of 2-methyl-5-formylpyridine hydrochloride in 75 ml of concentrated hydrochloric acid was heated at reflux for 1 hour. After working up as in Example 1 an oil is obtained which is taken up in methylene chloride-methanol then recrystallized from ethyl acetate to give 4-hydroxy-5-

[(6-methyl-3-pyridinyl)hydroxymethyl]-2-methylthiopyrimidine; 9.3 g (50%), m.p. 140°.

This compound (0.5 g) was mixed with 25 ml of glacial acetic acid and 0.12 g of zinc powder then heated at reflux for 16 hours. The mixture was cooled and filtered. The acetic acid was removed in vacuo. The residue was taken up in water and treated with 10% sodium hydroxide solution to separate 0.34 g of 5-[(6-methyl-3-pyridinyl)methyl]-2,4(1H,3H)-pyrimidinedione, m.p. 280°, MS(m/e) 217+218. This compound is then reacted in further steps as described in Example 1.

EXAMPLE 10

A mixture of 5 g (0.04 mol) of 2-methyl-5-formylpyridine, 5.29 g (0.04 mol) of 2-thiouracil and 50 ml of concentrated hydrochloric acid was heated overnight. The solution was neutralized with sodium bicarbonate. The organic material in the resulting precipitate was taken up in methanol which was then evaporated to give 4.53 g (45%) of 4-hydroxy-2-mercapto-5-[(6-methyl-3-pyridinyl)hydroxymethyl]pyrimidine [MS(m/e)250]. This compound (2 g) is treated with zinc-acetic acid as in Example 9 to give the same end product.

EXAMPLE 11

A mixture of 0.72 g (0.0044 m) of 4-(3-methoxy-2-pyridinyl)butylamine, 1.0 g (0.004 m) of 2-chloro-4-methoxy-5-[(6-methyl-3-pyridinyl)methyl]pyrimidine prepared as in Example 1, 0.47 g (0.0044 m) of anhydrous sodium carbonate and 15 ml of isopropanol was heated at reflux for 24 hours. The mixture was cooled, filtered and the filtrate evaporated to leave a brown oil. The product was partitioned between water and chloroform at pH 6.5. The chloroform was washed with water and dried. Evaporation gave 1.5 g of oil. This material was chromatographed over silica using chloroform and methanol/chloroform elution. The separated product fractions were combined and evaporated to give a colorless solid after trituration with aqueous ethanol; 0.86 g (m.p. 111°–112°) of 4-methoxy-5-[(6-methyl-3-pyridinyl)methyl]-2-[[4-(3-methoxy-2-pyridinyl)butyl]amino]-pyrimidine (m.p. 112°–3° from methanol/ethanol).

Anal. Calcd. for $C_{22}H_{27}N_5O_2$: C, 67.15; H, 6.92; N, 17.80. Found: C, 57.01; H, 6.96; N, 17.85. Infrared and nuclear magnetic resonance spectra check.

This material (0.1 g) is treated with hydriodic acid as in the last paragraph of Example 1 to give 2-[[4-(3-hydroxy-2-pyridinyl)butyl]amino]-5-[[6-methyl-3-pyridinyl)methyl]-4-(1H)-pyrimidinone dihyrochloride. 4-(3-Methyl-2-pyridinyl)butylamine and 4-(3-chloro-2-pyridinyl)butylamine are substituted in the above reaction sequence to give 2-[[4-(3-methyl-2-pyridinyl)butyl]amino]5-[(6-methyl-3-pyridinyl)methyl]-4-pyrimidinone or 2-[[4-(3-chloro-2-pyridinyl)butyl]amino]-5-[6-methyl-3-pyridinyl)methyl]-4-pyrimidinone.

EXAMPLE 12

A solution of 13.25 ml (0.0581 m) of 25% sodium methoxide in methanol was added dropwise to a mixture of 20 g (0.063 m) of 2-chloro-4-benzyloxy-5-[(6-methyl-3-pyridinyl)-methyl]-pyrimidine prepared as in Example 3 and 250 ml of toluene. The mixture is allowed to stir overnight at room temperature then washed with water and evaporated. The residual oil which was 2-methoxy-4-benzyloxy-5-[(6-methyl-3-pyridinyl)-methyl]-pyrimidine was dissolved in ethanol and hydrogenated over 0.6 g of 10% palladium on charcoal. After hydrogen absorption, the reaction mixture was filtered, concentrated to an oil which was taken up in methylene dichloride. Ether was added to give 8.4 g (59%) of 2-methoxy-5-[(6-methyl-3-pyridinyl)-methyl]-4-(1H)-pyrimidinone, m.p. 145°–147°.

Anal. Calcd. for $C_{12}H_{13}N_3O_2$: C, 62.32; H, 5.66; N, 18.17. Found: C, 62.11; H, 5.60; N, 17.99.

A mixture of 18 g (0.0779 m) of the 2-methoxypyrimidinone, 12.23 g (0.0779 m) of α-furylmethylthioethylamine and 50 ml of toluene was heated at reflux for 12 hours. Toluene (100 ml) was added to the cooled reaction mixture. The separated solid was washed with ethyl acetate and dried to give 20.69 g (74%) of 2-[[2-[(2-furylmethyl)thio]ethyl]amino]-5-[(6-methyl-3-pyridinyl)methyl]-4-(1H)-pyrimidinone.

Recrystallization from isopropanol-water gave 14.51 g (52%), m.p. 147°–152°, of purified compound.

Anal. Calcd. for $C_{18}H_{20}N_4O_2S$: C, 60.25; H, 5.65; N, 15.71; S, 8.99. Found: C, 60.29; H, 5.33; N, 15.43; S, 8.50.

Further reaction of this compound with bis(dimethylamino)methane using the procedure described in Example 3 gives the same end product as in that example.

Substitution of potassium ethoxide or sodium pentoxide in the above reaction gives 2-ethoxy or 2-pentyloxy-5-[(6-methyl-3-pyridinyl)-methyl]-4-(1H)pyrimidinones which can then be optionally condensed at position 2- of the pyrimidone with various heterocyclylmethylthioethylamines or heterocyclylbutylamines to give known end products having biological activity.

The 2-methoxypyrimidinone (1 g) is reacted with an equimolar quantity of 2-guanidino-4-[(2-aminoethyl)thiomethyl]thiazole in methanol and triethylamine to give 2-[[2-[(2-guanidinothiazolyl-4-yl-methyl)thio]ethyl]amino]-5-[(6-methyl-3-pyridinyl)methyl]-4-(1H)-pyrimidinone.

EXAMPLE 13

Substituting an equimolar quantity of 2-formylthiazole for 2-methyl-5-formylpyridine in the reaction sequence of Example 3 gives 5-[(2-thiazolyl)hydroxymethyl]-2,4(1H,3H)-pyrimidinedione, 5-[(2-thiazolyl)methyl]-2,4(1H,3H)-pyrimidinedione, 2,4-dichloro-5[(2-thiazolyl)methyl]pyrimidine, 2-chloro-4-benzyloxy-5-[(2-thiazolyl) methyl]pyrimidine, 2-[[2-[(2-furylmethyl)-thio]ethyl]amino]-4-benzyloxy-5-[(2-thiazolyl) methyl]-pyrimidine and the end product 4(1H)-pyrimidinone.

EXAMPLE 14

Substituting an equimolar quantity of 2-pyrimidinecarboxaldehyde in the reaction sequence of Example 3 gives 5-[(2-pyrimidinyl)hydroxymethyl]-2,4(1H,3H)-pyrimidinedione, 5-[(2-pyrimidinyl)methyl]-2,4(1H,3H)-pyrimidinedione, 2,4-dichloro-5-[(2-pyrimidinyl)methyl]pyrimidine, 2-chloro-4-benzyloxy-5-[(2-pyrimidinyl)methyl]pyrimidine, 2-[[2-[(2-furylmethyl)-thio]ethyl]amino]-4-benzyloxy-5-[(2-pyrimidinyl)-methyl]-pyrimidine and 2-[[2-[(2-furylmethyl)thio]ethyl]amino]-5-[(2-pyrimidinyl)methyl]-4(1H)-pyrimidinone.

EXAMPLE 15

Substituting an equimolar quantity of 4-pyridazinecarboxaldehyde in Example 3 gives 5-[(4-pyridazinyl)methyl]-2,4(1H,3H)-pyrimidinedione, 2,4-dichloro-5-[(4-pyridazinyl)methyl]pyrimidine, 2-chloro-4-benzyloxy-5-[(4-pyridazinyl)methyl]pyrimidine and 2-[[2-[(furylmethyl)thio]ethyl]amino]-5-[(4-pyridazinyl)-methyl]-4(1H)-pyrimidinone.

EXAMPLE 16

One tenth mole of 2-chloro-4-benzyloxy-5-[(6-methyl-3-pyridinyl)methyl]pyrimidine from Example 3 is reacted with sodium methoxide in toluene to give 80% of the 2-methoxy compound. Hydrogenolysis of this compound as in Example 3 gave 2-methoxy-5-[(6-methyl-3-pyrimidinyl)methyl]-4(1H)-pyrimidinone which was then condensed with α-furylmethylthioethylamine by heating in toluene at reflux for 7 hours to give 2-[[-[(2-furylmethyl)thio]ethyl]amino]-5-[(6-methyl-3-pyridinyl)methyl]-4(1H)pyrimidinone (62%). This compound is reacted with bis(dimethylamino)methane as in Example 3 to give the same end product. Other heterocyclic containing moieties are similarly inserted at the 2 and 5 positions of the 4-pyrimidinone.

What is claimed is:

1. The method of preparing a biheterocyclylpyrimidinone of the formula:

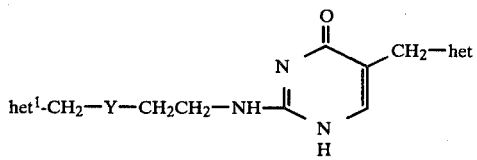

wherein:
Y is —CH$_2$— or —S—;
het is 2-pyridyl, 3-pyridyl, 4-pyridyl, 2-thiazolyl, 2-oxazolyl, 2-imidazole, 2-pyrimidyl or 2-pyrazyl all optionally C-substituted by methyl, ethyl, methoxy or ethoxy;
het$^1$ is 2- or 4-imidazolyl optionally C-substituted by C$_{1-3}$ alkyl, halo, trifluoromethyl or hydroxymethyl, 2-pyridyl optionally C-substituted by C$_{1-3}$ alkyl, C$_{1-3}$ alkoxy, halo, amino or hydroxy, 2-thiazolyl, 2-guanidino-4-thiazolyl, 3-isothiazolyl optionally C-substituted by chloro or bromo, 3-(1,2,5)-thiadiazolyl optionally C-substituted by chloro or bromo, 2-(5-amino-1,3,4-thiadiazolyl, 2-furanyl optionally 5-substituted by a R$_3$R$_4$N(CH$_2$)$_m$- or 2-thienyl optionally 5-substituted by a R$_3$R$_4$N(CH$_2$)$_m$-; and
R$_3$ and R$_4$ are C$_{1-3}$ lower alkyl or, when taken together with the nitrogen atom to which they are attached, pyrrolidino, piperidino or morpholinyl; and m is an integer of from 1-4; or a pharmaceutically acceptable acid addition salt thereof, comprising:

A. reacting in an acidic medium a compound of the formula het-CHO in which het is as defined above with a compound of the formula:

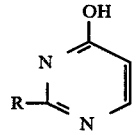

in which R is —OH, —SH or —SCH$_3$ to give a 5-heterocyclylhydroxymethylpyrimidine of the formula:

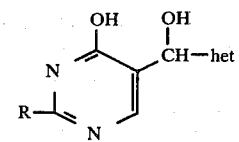

in which R and het are as defined above;

B. hydrogenolysis of said 5-heterocyclylhydroxymethylpyrimidine at the α-hydroxy position to give a 5-heterocyclylmethylpyrimidine of the formula:

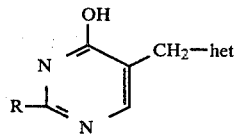

in which R is —OH and het is as defined above;

C. reacting said 5-heterocyclylmethylpyrimidine with haloesterifying agent to give a 2,4-dihalopyrimidine of the structure:

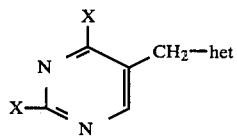

in which the X's are both either —Br or —Cl and het is as defined above.

D. reacting said 2,4-dihalopyrimidine with a substantially equimolar quantity of an alkali metal alkoxide to give a 2-halo-4-alkoxy or phenoxy pyrimidine of the formula:

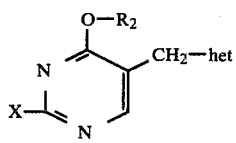

in which het and X are as defined above and R$_2$ is lower alkyl of 1-5 carbons, benzyl, allyl, phenyl, 2-methoxyethyl or 2,2,2-trichloroethyl;

E. condensing said 2-halo-4-alkoxy or phenoxypyrimidine with a compound of the formula:

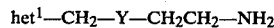

in which het$^1$ is as described above and Y is —S— or —CH$_2$— to give a triheterocyclic compound of the formula

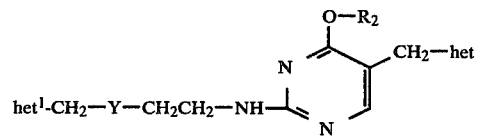

in which het, het$^1$, Y and R$_2$ are as described above;

F. reacting said triheterocyclic compound with a dealkylating agent to form the desired biherocyclylpyrimidinone; and optionally forming a pharmaceutically acceptable acid addition salt thereof.

2. The method of claim 1 in which the reaction in step A is carried out in a mineral acid medium with a pH of up to 5 and R and $R_1$ are —OH.

3. The method of claim 1 in which het is pyridinyl or 6-methyl-3-pyridinyl and R is —OH.

4. The method of claim 1 in which het is 6-methyl-3-pyridinyl, Y is —S— and $het^1$ is 2-furyl or 5-dimethylaminomethyl-2-furyl.

5. The method of claim 1 in which het is 6-methyl-3-pyridinyl, Y is —CH$_2$— and $het^1$ is 3-methoxy-2-pyridinyl.

6. The method of claims 1, 2, 3, 4 or 5 in which the reaction of step A is carried out in hydrochloric acid.

7. The method of claims 1, 2, 3, 4 or 5 in which X is —Cl, R is hydroxy, $R_2$ is benzyl and the reaction of step A is carried out in concentrated hydrochloric acid.

8. The method of claims 1, 2, 3, 4 or 5 in which $R_2$ is benzyl, X is —Cl and the reactions of steps A and B are carried out by reaction of hydriodic acid and acetic anhydride in a glacial acetic acid medium.

9. The method of preparing a compound of the formula:

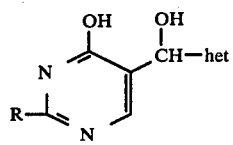

in which:
R is —OH, —SH or —SCH$_3$, and
het is 2-pyridyl, 3-pyridyl, 4-pyridyl, 2-thiazolyl, 2-oxazolyl, 2-imidazole, 2-pyrimidyl or 2-pyrazyl all optionally C-substituted by methyl, ethyl, methoxy or ethoxy, comprising reacting a compound of the formula:

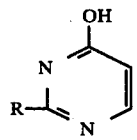

in which R is as defined above, with a compound of the formula, het-CHO, het being defined as above, in an acid medium in which the reactants are soluble at a temperature chosen from ambient up to reflux temperatures.

10. The method of claim 9 in which the medium is a mineral acid of pH up to 5.

11. The method of claim 9 in which het is pyridinyl and R is —OH.

12. The method of claim 9 in which het is 6-methyl-3-pyridinyl and R is —OH.

13. The method of claims 9, 10, 11 or 12 in which the acid medium is concentrated hydrochloric acid.

14. The method of claims 9, 10, 11 or 12 in which the reaction is run at reflux temperature in concentrated hydrochloric acid.

15. The method of claims 9, 10, 11 or 12 in which the reaction is run using hydriodic acid and acetic anhydride in glacial acetic acid and the product isolated is the α-dehydroxylated compound.

16. The method of claim 1 in which a methoxy or ethoxy substituent in het is converted to hydroxy during the reaction sequence.

17. The method of preparing 2-[[2-[[[5-[(dimethylamino)methyl]-2-furyl]methyl]thio]ethyl]amio]-5-[(6-methyl-3-pyridinyl)methyl]-4(1H)-pyrimidinone or one of its pharmaceutically acceptable acid addition salts comprising:

A. reacting in a mineral acid medium at a pH up to 5 uracil and 6-methyl-3-formylpyridine to form 5-[(6-methyl-3-pyridinyl)hydroxymethyl]-2,4(1H,3H)-pyrimidinedione.

B. hydrogenolysis of said hydroxymethylpyrimidinone to form 5-[(6-methyl-3-pyridinyl)methyl]-2,4(1H,3H)-pyrimidinedione.

C. reacting said methylpyrimidinedione with a haloesterifying agent to form a 2,4-dihalo-5-[(6-methyl-3-pyridinyl)methyl]pyrimidine.

D. reacting said dihalopyrimidine with a substantially equimolar quantity of an alkali metal benzylalcoholate or allyl alcoholate to give a 2-halo-4-allyloxy or benzyloxy-5-[(6-methyl-3-pyridinyl)methyl]pyrimidine.

E. reacting said allyloxy or benzyloxy pyrimidine with α-furylmethylthioethylamine in the presence of an acid binding agent to form 4-benzyloxy or 4-allyloxy-2-[[2-[(2-furylmethyl)thio]ethyl]amino]-5-[(6-methyl-3-pyridinyl)methyl]pyrimidine.

F. reacting said furylbenzyloxy or allyloxy pyrimidine with bis(dimethylamino)methane or formaldehydedimethylamine to form the Mannich base, 4-benzyloxy or 4-allyloxy-2-[[2-[[[5-[(dimethylamino)methyl]-2-furyl]methyl]thio]ethyl]amino]-5-[(6-methyl-3-pyridinyl)methyl]pyrimidine.

G. reacting said Mannich base with dilute acid to form 2-[[2-[[[5-[(dimethylamino)methyl]-2-furyl]methyl]thio]ethyl]amino]-5-(6-methyl-3-pyridinyl)methyl-4(1H)-pyrimidinone; and H. optionally forming a pharmaceutically acceptable acid addition salt by reacting said pyrimidinone with an excess of acid in an organic solvent.

* * * * *